United States Patent
Chan et al.

(10) Patent No.: US 6,461,386 B1
(45) Date of Patent: Oct. 8, 2002

(54) ANTIMICROBIAL TRANSFER SUBSTRATES AND METHODS OF USE THEREWITH

(75) Inventors: Marie S. Chan, Forest City, NC (US); Lawrence F. Kind, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/572,816

(22) Filed: May 17, 2000

(51) Int. Cl.⁷ .................. D06Q 1/02; D06M 13/322
(52) U.S. Cl. .................. 8/115.51; 8/115.6; 8/116.1; 8/188; 252/8.61; 252/8.63; 252/8.82; 428/340; 428/341; 428/342; 510/515
(58) Field of Search .............. 252/8.61, 8.63, 252/8.82; 8/115.51, 115.6, 116.1, 188; 428/340, 341, 342; 510/515

(56) References Cited

U.S. PATENT DOCUMENTS

| | | | |
|---|---|---|---|
| 4,460,644 A | | 7/1984 | Pavlich .................. 428/314.4 |
| 5,145,596 A | * | 9/1992 | Blank et al. .............. 252/106 |
| 5,221,574 A | | 6/1993 | Branch et al. ............. 428/289 |

FOREIGN PATENT DOCUMENTS

| | | |
|---|---|---|
| EP | 0 028 380 | 5/1981 |
| EP | 0 257 860 | 3/1988 |
| WO | 99/55390 | 11/1999 |
| WO | 99/65317 | 12/1999 |

* cited by examiner

Primary Examiner—Yogendra N. Gupta
Assistant Examiner—Derrick Hamlin
(74) Attorney, Agent, or Firm—Terry T. Moyer; William S. Parks

(57) ABSTRACT

Specific transfer methods and articles to impart a metal-ion based antimicrobial finish to recipient textile surfaces. Such treatments preferably comprise silver ions, particularly as constituents of inorganic metal salts or zeolites. In particular, the inventive method involves the application of a solid, inorganic antimicrobial material to a donor substrate (such as a dryer sheet), and the subsequent placement of such a substrate within a tumble drying machine containing textile fabrics and operating the machine. The donor substrate, upon contact with the recipient textile fabrics, transfers antimicrobially effective amounts of the metal-ion based compounds to such recipient fabrics thereby imparting at least a temporary antimicrobial finish over at least a portion of such fabrics. The donor substrates, with either the antimicrobial compound alone or mixed with standard tumble dryer additives (such as perfumes, fabric softeners, fiber lubricants, and the like) are also contemplated within this invention.

23 Claims, No Drawings

ANTIMICROBIAL TRANSFER SUBSTRATES AND METHODS OF USE THEREWITH

FIELD OF THE INVENTION

This invention relates to specific transfer methods and articles to impart a metal-ion based antimicrobial finish to recipient textile surfaces. Such treatments preferably comprise silver ions, particularly as constituents of inorganic metal salts or zeolites. In particular, the inventive method involves the application of a solid inorganic antimicrobial material to a donor substrate (such as a dryer sheet), and the subsequent placement of such a substrate within a tumble drying machine containing textile fabrics and operating the machine. The donor substrate, upon contact with the recipient textile fabrics, transfers antimicrobially effective amounts of the metal-ion based compounds to such recipient fabrics thereby imparting at least a temporary antimicrobial finish over at least a portion of such fabrics. The donor substrates, with either the antimicrobial compound alone or mixed with standard tumble dryer additives (such as perfumes, fabric softeners, fiber lubricants, and the like) are also contemplated within this invention.

DISCUSSION OF THE PRIOR ART

There has been a great deal of attention in recent years given to the hazards of bacterial contamination from potential everyday exposure. Noteworthy examples of such concern include the fatal consequences of food poisoning due to certain strains of *Eschericia coli* being found within undercooked beef in fast food restaurants; Salmonella contamination causing sicknesses from undercooked and unwashed poultry food products; and illnesses and skin infections attributed to *Staphylococcus aureus, Klebsiella pneumoniae*, yeast, and other unicellular organisms. With such an increased consumer interest in this area, manufacturers have begun introducing antimicrobial agents within various household products and articles. For instance, certain brands of polypropylene cutting boards, liquid soaps, etc., all contain antimicrobial compounds. The most popular antimicrobial for such articles is triclosan. Although the incorporation of such a compound within liquid or polymeric media has been relatively simple, other substrates, including the surfaces of textiles and fibers, have proven less accessible. There has a long-felt need to provide effective, durable, and long-lasting antimicrobial characteristics for textile surfaces, in particular on apparel fabrics, and on film surfaces. Such proposed applications have been extremely difficult to accomplish with triclosan, particularly when wash durability is a necessity (triclosan easily washes off any such surfaces). Furthermore, although triclosan has proven effective as an antimicrobial compound, the presence of chlorines within such a compound causes skin irritation which makes the utilization of such with fibers, films, and textile fabrics for apparel uses highly undesirable. Furthermore, there are commercially available textile products comprising acrylic and/or acetate fibers co-extruded with triclosan (for example Celanese markets such acetate fabrics under the name Microsafe™ and Acordis markets such acrylic fibers, under the tradename Amicor™). However, such an application is limited to those types of fibers; it does not work at all for natural fibers and specifically does not work for and/or within polyester, polyamide, cotton, spandex, etc., fabrics. Furthermore, this co-extrusion procedure is very expensive.

Silver-containing inorganic microbiocides have recently been developed and utilized as antimicrobial agents on and within a plethora of different substrates and surfaces. In particular, such microbiocides have been adapted for incorporation within melt spun synthetic fibers, as taught within Japanese unexamined Patent Application No. H11-124729, in order to provide certain fabrics which selectively and inherently exhibit antimicrobial characteristics. Furthermore, attempts have been made to apply such specific microbiocides on the surfaces of fabrics and yarns with little success from a durability standpoint. A topical treatment with such compounds has never been successfully applied as a durable finish or coating on a fabric or yarn substrate. Although such silver-based agents provide excellent, durable, antimicrobial properties, to date such is the sole manner available within the prior art of providing a long-lasting, wash-resistant, silver-based antimicrobial textile. However, such melt spun fibers are expensive to make due to the large amount of silver-based compound required to provide sufficient antimicrobial activity in relation to the migratory characteristics of such a compound within the fiber itself to its surface.

Attempts have been made in the past to apply an antimicrobial finish to a textile through transfer from a dryer sheet within a tumble dryer machine as taught within U.S. Pat. Nos. 5,145,596 and 5,221,574. The transfer is effectuated through the continuous and repetitive contact between the dryer sheet and the target textile. However, these particular methods disclose the transfer of gelled or liquefied (due to the friction and heat within the tumble dryer itself) organic treatments and/or compounds from the sheet to the textile. There is no mention of the transfer of inorganic solids (i.e., do not gel or liquefy) within these teachings. The patented transfer methods are performed quite easily due to the ability of such gelled or liquefied organic materials to effectively move from one surface to another through frictional contact.

Inorganic, solid antimicrobial materials (such as, for example, metal-ion based antimicrobials), as noted above, provide excellent antimicrobial characteristics, but have not been utilized on dryer sheets for transfer to textiles in the past. This past lack of interest was due to the difficulties involved with actually keeping the solid compound(s) in place on the dryer sheet surface. Furthermore, the transfer from dryer sheet to textile would also appear to be rather difficult since the transferred materials are solids and most likely possess rather high molecular weights. Even if the solids are contacted with the target textile, the ability for the treated surface to retain such solids during tumble drying seems nearly impossible. However, the ability to provide an antimicrobial treatment of a highly desirable and effective antimicrobial material to a target textile through a dryer sheet method would allow a consumer to apply such a desired treatment to textiles, such as clothing, linens, towels, even dry-clean only garments, and the like, through a simple, everyday procedure. To date, such a specific procedure incorporating such inorganic solid materials has not been accorded the industry by the prior art.

DESCRIPTION OF THE INVENTION

It is thus an object of the invention to provide a simple manner of effectively treating a fabric article with an antimicrobial inorganic solid treatment. Another object of the invention is to provide a non-yellowing antimicrobial. treatment through the utilization of a simple in-home or industrial-level laundry tumble dryer method. Yet another object of the invention is to provide a metal-ion-treated textile that is non-yellowing, non-irritating to skin, and which provides antimicrobial properties, through a simple, in-home application method.

Accordingly, this invention encompasses a method of applying an antimicrobial finish to a recipient textile substrate comprising the steps of (a) providing a donor substrate over at least a portion of which a solid inorganic antimicrobial material has been applied; and (b) frictionally contacting said donor substrate with a recipient textile surface (preferably, though not necessarily within an operating tumble dryer machine). Also, this invention encompasses a donor substrate comprising a transferable treatment comprising at least one solid inorganic antimicrobial material, and optionally comprising at least one other material selected from the group consisting of at least one fabric softening material, at least one perfume, at least one fragrance, at least one antistatic compound, and optionally sunscreen, antioxidant, and any mixtures thereof.

The term donor substrate is intended to encompass any standard type of fibrous, plastic, or foam substrate which can be frictionally contacted with a recipient fabric (such as within a standard or industrial tumble drying machine) and which has a lower affinity for the solid inorganic antimicrobial material than the recipient textile substrate. Preferably, such donor substrates are in the form of textiles or foams, and may be in two-dimensional (i.e., sheet) or three-dimensional form. More preferably such substrates are textile donor sheets, examples of which may be found within U.S. Pat. Nos. 5,929,026, 5,883,069, 5,470,492, and 4,735,738, 4,177,151, as merely examples. Such donor dryer sheets are generally paper, polyurethane foam, or textile in nature. Such textiles are comprised of any standard type of fiber. Preferably, such fibers are selected from polyester, polyamide, rayon, cotton, and any blends thereof. Furthermore, such sheets are constructed in any standard fashion, more particularly, and preferably of non-woven, woven, terry, or knit construction.

The term "frictionally contacting" is defined for this invention as the movement of at least one of the donor substrate and the recipient textile in contacting relation with the other (i.e., rubbing together) in order to effectuate at least some degree of transfer of the desired solid inorganic antimicrobial material from the donor substrate to the recipient textile. Such frictional contact may be performed, as merely one example, through simple hand rubbing of the recipient fabric with a donor substrate. Preferably, however, such contact is accomplished through operation of a closed tumble dryer machine containing both the donor substrate and the recipient textile.

The term "transferable" is intended to mean easily removed from the donor substrate and adhered to a recipient textile through a frictional contacting procedure (preferably, the aforementioned tumble dryer machine method). Thus, the treatment is adhered to the donor substrate at a very low adhesive level and friction will effectuate transfer to the recipient textile (with or without the presence of heat and/or moisture).

The term solid inorganic antimicrobial material is intended to encompass any solid compound which is primarily inorganic in nature (some organic component is permitted, although the primary antimicrobial portion must be inorganic), is a solid at standard temperature and pressure, and which exhibits antimicrobial activity. More particularly, such a material is selected from any metal-ion containing compounds. Preferably, such material is an metal-based ion-exchange compound, a metal-based zeolite, a metal salt, a metal oxide, a metal hydroxide, and any combinations thereof More preferably, the material possess a transition metal ion, including, for example, silver ions, zinc ions, copper ions, magnesium, and any combination thereof. Most preferably, the material is a silver-based ion exchange material or zinc oxide. The specific-silver-based ion exchange material is an antimicrobial silver zirconium phosphate available from Milliken & Company, under the tradename ALPHASAN®. Other potentially preferred silver-containing solid inorganic antimicrobials in this invention is a silver-substituted zeolite available from Sinanen under the tradename ZEOMIC® AJ, or a silver-substituted glass available from Ishizuka Glass under the tradename IONPURE®, may be utilized either in addition to or as a substitute for the preferred species. Other possible compounds, again without limitation, are silver-based materials such as AMP® T558 and MICROFREE®, both available from DuPont, as well as JMAC®, available from Johnson Matheny. Such solid inorganic based compounds are applied to a donor sheet substrate via a bath composition (through immersion, dip-coating, knife-coating, spraying, printing, and the like). Generally, such a metal compound is added in an amount of from about 0.01 to 70% by total weight of the particular treatment composition; preferably from about 0.05 to about 50%; more preferably from about 8 to about 35%; and most preferably from about 8 to about 20%. The silver-ion compound is then added to the target donor sheet in amounts of between 0.3 g and 7.5 g to provide the best antimicrobial effectiveness on the recipient fabric surface. Preferably this metal compound add-on weight is about 2.5 g. The bath composition itself (including necessary thickeners) is added to the substrate in an amount of about 1 to about 25 grams in total. Such an addition is easily measured through weighing the donor sheet before and after application of the antimicrobial treatment. The thickener is utilized to keep the desired solid inorganic antimicrobial materials suspended during application to the substrate (and to keep the solid inorganic antimicrobial materials in place on the selected donor sheet surface). Preferably, such thickeners are selected from the group consisting of cellulose-based, water soluble thickening agents, including, without limitation, hydroxyethylcellulose, carboxylmethylcellulose, hydroxypropylcellulose, or other thickeners such as, without limitation, guar gums, alginates, and the like. Such thickeners are generally mixed with the solid inorganic antimicrobial materials in a mixing vessel and then applied to the donor sheet surface. Such application may be accomplished through padding, coating, spraying, dipping, foam application and the like. Preferably, pad or knife coating is utilized for such application. The mixture of thickener to antimicrobial material is from about 0.1 to 5% thickener and from about 0.01 to about 70% solid inorganic antimicrobial, all by total weight of the bath composition, with any remainder being water and other standard low-level additives as noted above; preferably, this mixture is from about 0.1 to 3% thickener and from about 1 to about 50% antimicrobial; more preferably, from about 0.5 to about 3% thickener and from about 1 to about 40% antimicrobial; most preferably, this mixture is from about 1 to 3% thickener and from about 1 to 35% antimicrobial.

The particular antimicrobial material should exhibit an acceptable log kill rate after 24 hours in accordance with the AATCC Test Method 100-1983. Such an acceptable level log kill rate is tested for *Staphylococcus aureus* or *Klebsiella pneumoniae* of at least 0.1 increase over baseline. Alternatively, an acceptable level will exist if the log kill rate is greater than the log kill rate for non-treated (i.e., no solid inorganic antimicrobial added) recipient fabrics (such as about 0.5 log kill rate increase over control, untreated fabrics). Preferably these log kill rate baseline increases are at least 0.3 and 0.3, respectively for *S. aureus* and *K.*

*pneumoniae*; more preferably these log kill rates are 0.5 and 0.5, respectively; and most preferably these are 1.0 and 1.0, respectively. However, log kill rates which are negative in number are also acceptable for this invention as long as such measurements are better than that recorded for correlated non-treated textiles. In such an instance, the antimicrobial material present on the textile at least exhibits a hindrance to microbe growth. Such an invention also encompasses the different methods of producing such a treated substrate.

The term tumble dryer encompasses any standard rotary drying machine, either for use in a person's home or on an industrial level used either to dry wet laundry (through exposure to sufficient heat, such as from about 50 to about 200° F.) or to treat other non-laundered fabrics either at such elevated temperatures or simply operating the machine at a lower temperature. The standard drying procedure followed is that specific portion of AATCC Test Method 130-1989. Also, included in such a list of non-laundered fabrics are dry-clean only fabrics cleaned or freshened through the utilization of certain chemicals within an enclosure and tumble dried at either room temperature or such an elevated temperature. Such dry-clean only treatments are disclosed within U.S. Pat. Nos. 5,630,848, 5,591,236, 5,951,716.

Nowhere within the prior art has such a specific method or specific donor sheet been disclosed, utilized, or fairly suggested. The closest art, U.S. Pat. Nos. 5,154,947 and 5,221,574, all noted and incorporated herein previously, only concern organic antimicrobial agents transferred through dryer sheet articles to target textiles in a dryer machine.

Any target recipient fabric may be treated through the inventive method and/or contacted with the inventive donor sheet. Thus, natural (cotton, wool, and the like) or synthetic fibers (polyesters, polyamides, polyolefins, acrylics, rayon and the like) may constitute the target substrate, either by itself or in any combinations or mixtures of synthetics, naturals, or blends or both types. As for the synthetic types, for instance, and without intending any limitations therein, polyolefins, such as polyethylene, polypropylene, and polybutylene, halogenated polymers, such as polyvinyl chloride, polyesters, such as polyethylene terephthalate, polyester/polyethers, polyamides, such as nylon 6 and nylon 6,6, polyurethanes, as well as homopolymers, copolymers, or terpolymers in any combination of such monomers, and the like, may be utilized within this invention. Nylon 6, Nylon 6,6, polypropylene, and polyethylene terephthalate (a polyester) are particularly preferred. Additionally, the target fabric may be coated with any number of different films as well, including polyurethanes, polyethers, polyolefins, polyhalides, and the like.

The selected donor substrate may comprise any fabric comprising individual fibers or yarns of any typical source for utilization within fabrics, including natural fibers (cotton, wool, ramie, hemp, linen, and the like), synthetic fibers (polyolefins, polyesters, polyamides, polyaramids, acetates, rayon, acylics, and the like), and inorganic fibers (fiberglass, boron fibers, and the like). The yarn or fiber may be of any denier, may be of multi- or mono-filament, may be false-twisted or twisted, or may incorporate multiple denier fibers or filaments into one single yarn through twisting, melting, and the like. The target fabrics may be produced of the same types of yarns discussed above, including any blends thereof. Such fabrics may be of any standard construction, including knit, woven, or non-woven forms. As noted above, the donor substrate may also be comprised of any standard foam components for tumble dryer transfer to recipient textiles. Such foams may be (preferably) polyurethane in nature, although other foams, such as polyethers, polyesters, and polyolefins, may also be present and/or utilized.

The donor substrate may also include other additives or components for transfer to the target fabrics. Thus, the sheet may also comprise, without limitation, fabric softening materials (including, without limitation, materials which provide static dissipation, yarn lubrication, and any other standard softening compounds), perfumes, fragrances, cleaning solvents (such as, without limitation, etherified propanol solvents an other low-odor cleaning liquids), detersive surfactants (amine oxides, alkylethoxy sulfates, ethoxylated alcohols, and mixtures thereof, as merely a few non-limiting examples), emulsifiers (polyacrylates, as merely one non-limiting example), antistatic compounds, soil release agents, optical brighteners, odor control agents, fiber lubricants, antioxidants, sunscreens and any mixtures thereof. Particular fabric softening or conditioning materials include quaternary ammonium compounds, imidazolinium compounds, amines, amine oxides, and like, or amine salt selected from the group consisting of oleyldimethylamine stearate, dioleylmethylamine stearate, linoleyldimethylamine dilinoleylmethylamine stearate, stearate, stearyldimethylamine distearylmethylamine myristate, stearate, stearyldimethylamine palmitate, distearylmethylamine palmitate, distearylmethylamine laurate, distearylmethylamine oleate, and mixtures thereof. Such compounds are disclosed within U.S. Pat. Nos. 4,177,151, 4808086, 4849257, 5,470,492, 5,883,069. Or amino functional silicones, polydiorganosiloxanes and nonionic softeners as disclosed in U.S. Pat. Nos. 5,300,238 and 4,767,548. Such compounds may be applied in amounts of from about 0.01 to about 75% owf; preferably, from about 0.1 to about 50%; more preferably, from about 5 to about 50% owf. These may be applied on either side of the donor sheet, but preferably applied on one side of the donor sheet while the antimicrobial is applied to the other side. The other listed potential additives or components may be applied on the same side of the donor sheet as the fabric softening material or, possibly, over both sides of the sheet, or on the same side as the antimicrobial material (if such is applied to one side only).

As noted above, dry-clean only garments may be treated with the inventive dryer sheets as well as standard laundered fabrics. The sheets may comprise solely an antimicrobial, such as the desired solid inorganic antimicrobial either alone or with other liquid or solid organic antimicrobial compounds; or, these sheets may include cleaning solvents, odor-reduction compounds, detersive surfactants, and the like (i.e., those compounds taught within U.S. Pat Nos. 5,630,828, 5,591,236, and 5,951,716, pertaining to such in-home dry-cleaning methods).

The preferred embodiments of these alternatives fabric treatments are discussed in greater detail below.

DESCRIPTION OF THE PREFERRED EMBODIMENTS

Examples of particularly preferred compounds within the scope of the present invention are set forth below.

Donor Substrate Production

The preferred inventive donor substrates, particularly donor fabric sheets, may be woven, non-woven, or terry fabrics, comprised of cottons, polyesters (PE), cotton/polyester blends, or polyester/rayon blends (PE/R). The preferred non-woven sheet is 5"×11" in its dimensions and is constituted with polyester fibers. The preferred woven sheet is 13"×18" in its dimensions and is constituted with polyester fibers as well. The preferred dimensions are not particularly special in this situation; any size sheet which facilitates placement and utilization within a clothes drying machine may work.

Coating baths were prepared for the two preferred sheets noted above. These baths comprised 1% by weight of a hydroxyethyl cellulose thickener, from about 8 to about 35% by weight of ALPHASAN®, and the remainder water. Ammonia was also added in order to adjust the pH of the bath to about 8.0, but only as needed. Similar bath compositions were provided with the same amounts of components, only with a modification concerning the active antimicrobial ingredient. Thus, other, less preferred, but viable baths comprising about 10% by weight of a) ZEOMIC®, b) AMP® T558, c) JMAC® (Silver chloride/Titanium dioxide mixture), d) IONPURE®, and e) zinc oxide, all separately mixed with about 1% of hydroxyethylcellulose were also provided. Six different samples of the above non-woven and woven fabrics were then coated with these different bath compositions. The most preferred method of performing such a step was a dip/pad procedure wherein the donor sheet was immersed within the bath for about 1 minute and squeezed through a pad mangle at 40 psi. The wet pick-up of the particular fabric sheet was from about 70 to about 140%. Air drying was then undertaken for about 1 hour to permit adherence of the silver and/or zinc antimicrobial to the target sheet surface. If necessary, the coated fabric sheet may also be cured at a temperature of about 300° F. for about one minute (other coating methods include knife coating followed by air drying and/or curing or knife coating followed by pad squeezing and air drying and/or curing).

Non-woven sheets were also produced with fabric softeners either applied on the opposite side of the target donor sheet or as a mix with the antimicrobial compounds. Thus, three sheets, were produced with fabric softener constituents present. A separate non-woven polyester/rayon sheet with the ALPHASAN®-containing composition from above was produced; the opposite side was coated with a thickened composition comprising about 50% by weight of a diamidoamine-based quaternary ammonium salt (Varisoft® 222LT from Witco—methyl bis(oleylamidoethyl)-2-hydroxyammonoium methylsulfate, modified). The same type of sheet was produced with the fabric softener being triethanolamine ester quaternary ammonium (Varisoftd® WE-16 from Witco—di-(tallow carboxyethyl) hydroxyethyl methyl ammonium methosulfate). A third sheet comprised imidazolinium quaternaries (Accosoft® 808 from Stepan— (tallow carboxyethyl)-dimethyl imidazolinium methylsulfate). It is understood, again, that these listed fabric softeners are merely preferred embodiments and are not intended to limit the available fabric softeners within this invention. The compositions were all knife-coated with the softener component first (to add-on about 1.5 grams of softener material on the sheet surface). After air drying, the antimicrobial component was then knife coated and air dried on the opposite side of the sheet. Also, a preprepared BOUNCE®-brand (Procter & Gamble) dryer sheet comprising fabric softener material was also knife-coated within the above-noted thickened antimicrobial (ALPHASAN®) bath formulation and allowed to air-dry for about 1 hour.

One further non-woven polyester/rayon sheet was coated with a mixture of the Accosoft® and ALPHASAN® components listed above as well. Two separate mixes of 1) softener and 2) antimicrobial, were first prepared, mixed together, and then knife coated with pad squeeze on the sheet surface. The resultant coating was then air dried and cured (as noted above). The softener composition, 1), comprised about 27.8% of the Accosoft® softener, about 1.8% of a 25% aqueous calcium chloride, and about 70.4% of water (all percentages based upon weight within the composition). The antimicrobial mix comprised the same mixture as added to the sheet surface, above. This mix and the softener mix were then admixed in a 50:50 ratio (by weight) and applied to a non-woven polyester/rayon sheet through a knife coat-pad squeeze procedure. The resultant coating was then air dried and cured for about 1 minute.

Additionally, a dryer (freshening) sheet was taken from a DRYEL®-brand in-home dry-cleaning kit (available from The Procter & Gamble Company). Liquid was squeezed from the sheet, the sheet was then dip-coated (then squeezed and air-dried for 1 hour) with the above-noted ALPHASAN® thickener composition, and the previously removed liquid was poured back over the dip-coated sheet.

In tabular form, these specific aforementioned inventive sheets, as well as lower level ALPHASAN® coated donor sheets, were produced as follows:

TABLE 1

Inventive Dryer Sheet Production
(all with 1% by weight of a Hydroxyethylcellulose Thickener)

| Ex. | Sheet Type | Antimicrobial (% by weight) | Additives (% by weight) |
|---|---|---|---|
| 1 | Woven (PE) | ALPHASAN ® (35%) | |
| 2 | Non-Woven (PE) | ALPHASAN ® (35%) | |
| 3 | Woven (PE) | ALPHASAN ® (31%) | |
| 4 | Woven (PE) | ALPHASAN ® (28%) | |
| 5 | Woven (PE) | ALPHASAN ® (25%) | |
| 6 | Terry Cloth | ALPHASAN ® (20%) | |
| 7 | Woven (PE) | ALPHASAN ® (14%) | |
| 8 | Woven (PE) | ALPHASAN ® (18%) | |
| 9 | Woven (PE) | ALPHASAN ® (9%) | |
| 10 | Woven (PE) | ALPHASAN ® (1%) | |
| 11 | Woven (PE) | ZEOMIC ® (10%) | |
| 12 | Woven (PE) | AMP ® T558 (10%) | |
| 13 | Woven (PE) | JMAC ® (10%) | |
| 14 | Woven (PE) | IONPURE ® (10%) | |
| 15 | Woven (PE) | Zinc Oxide (10%) | |
| 16 | Non-Woven (PE/R) | ALPHASAN ® (30%) | VARISOFT ®222-LT(23% opp.side) |
| 17 | Non-Woven (PE/R) | ALPHASAN ® (30%) | VARISOFT ®WE16(75% opp.side) |
| 18 | Non-Woven (PE/R) | ALPHASAN ® (30%) | ACCOSOFT ®808(27.8% opp.side) |
| 19 | BOUNCE ®brand | ALPHASAN ® (30%) | |

TABLE 1-continued

Inventive Dryer Sheet Production
(all with 1% by weight of a Hydroxyethylcellulose Thickener)

| Ex. | Sheet Type | Antimicrobial (% by weight) | Additives (% by weight) |
|---|---|---|---|
| 20 | Non-Woven (PE/R) | ALPHASAN ® (30%) | ACCOSOFT ®808 (27.8% mix) |
| 21 | DRYEL ®-brand | ALPHASAN ® (8%) | |

Clothes Dryer Utilization

These individual sheets were then introduced within a standard Kenmore in-home clothes dryer (in accordance with AATCC Test Method 130-1989, as noted previously) with either cotton terry cloth towels or 65/35 polyester/cotton shirting fabrics (either non-laundered, and thus dry, or laundered, and thus damp) or orlon-based dry clean only fabrics. Initially, a non-coated sheet was introduced as a control. During each separate test, two selected fabric substrates were added to a dummy load (for a total of 4 pounds of fabric) within the dryer. The dryer was then operated at temperatures between about 70 and 180° F. (preferably about 110° F.) for about 30 minutes. It is noted that neither heat nor moisture is necessary to effectuate transfer of the antimicrobial to the fabric surface; only intimate and repeated contact within the operable dryer machine is required for such an antimicrobial application. Humidity and moisture may also alternatively be exhibited within the operating dryer machine. Although 0% humidity is possible, a level from about 30 to about 100% is most preferred. This moisture may be supplied solely by wet laundry itself.

Taking the Example 1 dryer sheet from TABLE 1 and subjecting the particular terry cloth towels to a drying process at about 110° F. for roughly 30 minutes, garnered the following tabulated log kill data for *K. pneumoniae* (in accordance with AATCC Test Method 100-1993 for 24 hours; it should be well appreciated by the ordinarily skilled artisan that log kill rates are generally average readings and, although highly reliable, will not always follow predictable and constant trends):

TABLE 2

| Process Conditions | Log Kill Rate |
|---|---|
| Heat and moisture | 407 |
| Moisture Only | 1.93 |
| Heat Only | 3.47 |
| No Heat or Moisture | 4.45 |

Apparently, the best overall effect is a relatively cool, dry atmosphere within the selected dryer machine. However, the efficacy of the other conditions shows the viability of this invention under different conditions as well.

Further examples from TABLE 1 were then tested for antimicrobial efficacy. The following TABLE shows the log kill measurements (*K. pneumoniae*) for 65/35 polyester/cotton shirting (Examples 3–5 and 6–9) and damp terry cloth towels (Examples 6 and 10–14) dried at about 110° F. in the presence of the correlated example sheets. The results are tabulated as follows:

TABLE 3

| Example | Log Kill Rate |
|---|---|
| 3 | 2.20 |
| 4 | 4.10 |
| 5 | 4.10 |
| 6 | 4.08 |
| 7 | 4.10 |
| 8 | 3.50 |
| 10 | 2.20 |
| 11 | 4.51 |
| 12 | 3.81 |
| 13 | 4.51 |
| 14 | 3.46 |
| 15 | 1.53 |

Example 6 was also tested for *S. aureus* log kill rate. This was measured (in accordance with the AATCC Test Method 100-1993, again for 24 hours exposure) to be about 3.22.

The silver-based antimicrobials (3–8 and 10–14) performed very well in antimicrobial efficacy, although, the non-ALPHASAN®-treated sheets did not perform as well as the preferred ALPHASAN®-treated sheets. The zinc oxide-coated sheet was less efficacious than the silver-based counterparts; however, such a specific coating is still viable as a desirable antimicrobial transfer donor sheet and method.

Fabric softener-containing dryer sheets from TABLE 1 were then tested for antimicrobial transfer to damp terry cloth towels at a temperature of about 110° F. in the same type of dryer as noted above. Example 21 (the DRYEL®-brand ALPHASAN® treated sheets) was utilized in both a wet (21a) and dry (21b) method on orlon dry-clean only fabric. In accordance with DRYEL® requirements, the recipient fabric was placed within an enclosure bag (with three dummy garments) and the freshening/antimicrobial sheet. After treatment and exposure to the inventive donor sheet, log kill measurements for *K. pneumoniae* were made for the recipient fabrics in accordance with AATCC Test Method 100-1993 (for 24 hours exposure). The results are tabulated as follows (with comparative results for a preprepared BOUNCE®-brand dryer sheet without solid inorganic antimicrobial additives, a non-woven polyester/rayon blends sheets produced with only a 27.8% by weight coating of ACCOSOFT® 808 applied, and a drying step without any donor sheet added):

TABLE 4

| Example | Log Kill Rates |
|---|---|
| 16 | 0.55 |
| 19 | −0.66 |
| 21 | −0.14 |
| 21a | 4.47 |
| 21b | 2.72 |
| BOUNCE ® only | −0.84 |
| ACCOSOFT ® only | −0.66 |
| None | −1.46 |

The best performance was clearly provided by the solid inorganic antimicrobial-treated DRYEL®-brand sheets.

However, the antimicrobial efficacy of the other additive (fabric softener) containing sheets, although low in comparison to the other sheets, was still acceptable to impart some degree of antimicrobial activity to the target fabrics, or, at least, to hinder the growth of microbes on the fabric surface.

Donor Substrate and Recipient Textile Antimicrobial Durability

Surprisingly, the inventive donor substrates exhibit reusable durability. For example, donor substrate Example 9, from TABLE 1, above, exhibited the following K. pneumoniae log kill rates (AATCC Test Method 100-1993, 24 hours) upon multiple usage in a tumble dryer operation for 65/35 polyester/cotton fabric shirting recipient textiles:

TABLE 5

| Number of Uses | Log Kill Rates |
| --- | --- |
| 1 | 3.40 |
| 2 | 4.15 |
| 3 | 2.95 |
| 4 | 3.95 |
| 5 | 3.30 |

Thus, the donor substrate was reusable for at least five drying procedures. Such reusability should be more prevalent when greater amounts of solid inorganic antimicrobial material are initially present on the donor substrate.

Also surprisingly, the recipient fabrics exhibited a certain low degree of antimicrobial wash durability as well. For instance, the donor substrate of Example 1 from TABLE 1 was tumble dried with cotton terry cloth towel sample fabrics in accordance with the heat and moisture conditions of TABLE 2 (thereby exhibiting an initial log kill rate for K. pneumoniae as measured under AATCC Test Method 100-1993, 24 hours, of 4.21). After two subsequent washings and dryings (without more antimicrobial treatments at all) in accordance with AATCC 103-1989, the recipient sample fabrics exhibited the following log kill rates:

TABLE 6

| Number of Washes | Log Kill Rates |
| --- | --- |
| 1 | 3.44 |
| 2 | 3.09 |

Thus, further antimicrobial treatments to recipient fabrics may be unnecessary on a weekly or perhaps monthly basis (at least for successive launderings), particularly with greater transferred add-on amounts of solid inorganic antimicrobial material on a recipient textile.

Lightfastness of Certain Samples

Certain recipient fabric samples treated with different amounts of antimicrobial (or none, with fabric softener added, as controls) were analyzed for the lightfastness of the color exhibited by the treated fabrics after dryer-effectuated application of the desired solid inorganic antimicrobial from a donor sheet. For a further discussion and explanation of this testing procedure, see Billmeyer, F. W., et al., *Principles of Color Technology*, 2nd Edition, pp. 62–64 and 101-04. Color lightfastness is generally calculated by the following equation:

$$\Delta E^* = ((L^*_{initial} - L^*_{exposed})^2 + (a^*_{initial} - a^*_{exposed})^2 + (b^*_{initial} - b^*_{exposed})^2)^{1/2}$$

wherein $\Delta E^*$ represents the difference in color between the fabric upon initial latex coating and the fabric after the above-noted degree of ultra violet exposure. $L^*$, $a^*$, and $b^*$ are the color coordinates; wherein $L^*$ is a measure of the lightness and darkness of the colored fabric; $a^*$ is a measure of the redness or greenness of the colored fabric; and $b^*$ is a measure of the yellowness or blueness of the colored fabric. A low $\Delta E^*$ shows excellent lightfastness for the tested fabric; a $\Delta E^*$ greater than about 6.5 is unacceptable and shows a yellowing tendency for the treated fabric. The particular recipient samples were subjected to a Xenon Arc Lamp Test at 225 kJ/m$^2$ for both 20 and 40 hours to analyze the yellowing characteristics of the treated fabric. Modified coating baths from Example 1, above, were utilized to coat the donor sheet. These modifications solely comprised of a reduction in antimicrobial to 9% and 20% add-on weight on the fabric (the same thickener and amount thereof was utilized). Different fabrics were treated in the dryer machine (65/35 polyester cotton and cotton terry cloth towels) in this lightfastness analysis. The results are thus tabulated as follows:

TABLE 7

| % of ALPHASAN ® on on Donor Sheet | Recipient Fabric | $\Delta E^*$ at 20 hours | $\Delta E^*$ at 40 hours |
| --- | --- | --- | --- |
| 20% owf | 65/35 poly/cotton | 1.34 | 1.82 |
| 9% owf | 65/35 poly/cotton | 1.03 | 1.23 |
| 20% owf | cotton terry cloth | 5.29 | 6.43 |
| (control with softener) | 65/35 poly/cotton | 0.48 | 0.72 |
| (control with softener) | cotton terry cloth | 3.40 | 4.70 |

Clearly and surprisingly, the silver-treated fabrics exhibited acceptable lightfastness Characteristics, particularly in comparison with the fabrics treated with softener-containing sheets alone.

There are, of course, many alternative embodiments and modifications of the present invention which are intended to be included within the spirit and scope of the following claims.

What we claim is:

1. A method of applying an antimicrobial finish to a recipient textile substrate comprising the steps of
    (a) providing a donor substrate, at least a portion to which a solid inorganic antimicrobial material has been applied, and wherein said donor substrate optionally comprises at least one other material selected from the group consisting of at least one fabric softening material, at least one perfume, at least one fragrance, at least one antistatic compound, soil release agents, optical brighteners, odor control agents, fiber lubricants, antioxidants, sunscreens and any mixtures thereof; and
    (b) frictionally contacting said donor substrate with a recipient textile surface.

2. The method of claim 1 wherein the frictional contacting of step "b" is performed within an operating tumble dryer machine.

3. The method of claim 1 wherein said solid inorganic antimicrobial material comprises at least one metal-ion based antimicrobial compound.

4. The method of claim 3 wherein said metal-ion based antimicrobial compound is selected from a metal-based ion exchange material, a metal-containing zeolite, a metal oxide, a metal hydroxide, and metal salt, and any combination thereof.

5. The method of claim 4 wherein said metal is selected from the group consisting of at least one of the transition metal ions.

6. The method of claim 5 wherein said transition metals are selected from the group consisting of silver ions, zinc ions, copper ions, magnesium ions, and any mixtures thereof.

7. The method of claim 6 wherein said metal-ion antimicrobial compound is selected from the group consisting of a silver-based ion exchange compound, zinc oxide, and any combination thereof.

8. The method of claim 1 wherein said donor sheet is constructed of fibers selected from the group consisting of polyester, rayon, acrylic, polyamide, cotton, and any blends thereof.

9. The method of claim 1 wherein said donor sheet is woven, non-woven, or knit in construction.

10. The method of claim 9 wherein said donor sheet is constructed of fibers selected from the group consisting of polyester, rayon, acrylic, polyamide, cotton, and any blends thereof.

11. The method of claim 2 wherein step "b" is performed at a temperature range of 70° F. to 180° F.

12. The method of claim 1 wherein said donor substrate comprises at least one other material selected from the group consisting of at least one fabric softening material, at least one perfume, at least one fragrance, at least one antistatic compound, soil release agents, optical brighteners, odor control agents, fiber lubricants, antioxidants, sunscreens and any mixtures thereof.

13. The method of claim 12 wherein said donor substrate comprises a fabric softening compound.

14. A tumble dryer donor substrate comprising a transferable treatment comprising at least one solid inorganic antimicrobial material, and optionally comprising at least one other material selected from the group consisting of at least one fabric softening material, at least one perfume, at least one fragrance, at least one antistatic compound, soil release agents, optical brighteners, odor control agents, fiber lubricants, antioxidants, sunscreens and any mixtures thereof.

15. The substrate of claim 14 wherein said metal-ion based antimicrobial compound is selected from a metal-based ion exchange material, a metal-containing zeolite, a metal oxide, a metal hydroxide, and metal salt, and any combination thereof.

16. The substrate of claim 15 wherein said metal is selected from the group consisting of at least one of the transition metal ions.

17. The substrate of claim 16 wherein said transition metals are selected from the group consisting of silver ions, zinc ions, copper ions, magnesium ions, and any mixtures thereof.

18. The substrate of claim 17 wherein said metal-ion antimicrobial compound is selected from the group consisting of a silver-based ion exchange compound, zinc oxide, and any combination thereof.

19. The substrate of claim 14 wherein said donor substrate is constructed of fibers selected from the group consisting of polyester, polyamide, rayon, acrylic cotton, and any blends thereof.

20. The substrate of claim 14 wherein said donor substrate is woven, non-woven, or knit in construction.

21. The substrate of claim 20 wherein said donor substrate is constructed of fibers selected from the group consisting of polyester, polyamide, rayon, acrylic, cotton, and any blends thereof.

22. The substrate of claim 14 wherein said donor substrate comprises at least one other material selected from the group consisting of at least one fabric softening material, at least one perfume, at least one fragrance, at least one antistatic compound, soil release agents, optical brighteners, odor control agents, fiber lubricants, antioxidants, sunscreens and any mixtures thereof.

23. The substrate of claim 22 wherein said donor substrate comprises a fabric softening compound.

* * * * *